US012779030B2

(12) United States Patent
Shen et al.

(10) Patent No.: US 12,779,030 B2
(45) Date of Patent: Nov. 3, 2026

(54) RHABDOVIRUS-NEGATIVE SPODOPTERA FRUGIPERDA INSECT CELL LINE, AND SCREENING, IDENTIFICATION AND APPLICATION THEREOF

(71) Applicant: WestVac Biopharma Co., Ltd., Chengdu (CN)

(72) Inventors: Guobo Shen, Chengdu (CN); Xiawei Wei, Chengdu (CN); Yuquan Wei, Chengdu (CN); Li Yang, Chengdu (CN)

(73) Assignee: WestVac Biopharma Co., Ltd., Chengdu (CN)

( * ) Notice: Subject to any disclaimer, the term of this patent is extended or adjusted under 35 U.S.C. 154(b) by 112 days.

(21) Appl. No.: 18/556,556

(22) PCT Filed: Dec. 23, 2022

(86) PCT No.: PCT/CN2022/141358
§ 371 (c)(1),
(2) Date: Oct. 20, 2023

(87) PCT Pub. No.: WO2023/165231
PCT Pub. Date: Sep. 7, 2023

(65) Prior Publication Data

US 2024/0207390 A1 Jun. 27, 2024

(30) Foreign Application Priority Data

Mar. 1, 2022 (CN) ........................ 202210194024.X

(51) Int. Cl.

| | |
|---|---|
| ***A61K 39/215*** | (2006.01) |
| ***C07K 14/005*** | (2006.01) |
| ***C12N 5/07*** | (2010.01) |
| ***C12N 7/00*** | (2006.01) |
| *C12R 1/91* | (2006.01) |

(52) U.S. Cl.
CPC .......... *A61K 39/215* (2013.01); *C07K 14/005* (2013.01); *C12N 5/0601* (2013.01); *C12N 7/00* (2013.01); *C12N 2770/00022* (2013.01); *C12N 2770/20034* (2013.01); *C12R 2001/91* (2021.05)

(58) Field of Classification Search
CPC ...... C12R 2001/91; C12N 2770/20022; C12N 5/06; C12N 5/10; C12N 2800/105
See application file for complete search history.

(56) References Cited

U.S. PATENT DOCUMENTS

| | | | |
|---|---|---|---|
| 11,384,364 | B2 | 7/2022 | Zolotukhin et al. |
| 11,473,055 | B2 | 10/2022 | Maghodia et al. |
| 2018/0094236 | A1 | 4/2018 | Granados et al. |

FOREIGN PATENT DOCUMENTS

| | | | |
|---|---|---|---|
| CN | 108603176 | A | 9/2018 |
| CN | 109311932 | A | 2/2019 |
| CN | 110423726 | A | 11/2019 |

OTHER PUBLICATIONS

Paul, Fundamental Immunology, 3rd Edition, 1993, pp. 292-295 (Year: 1993).*
Bendig, M. M., Humanization of Rodent Monoclonal Antibodies by CDR Grafting, 1995, Methods: A Companion to Methods in Enzymology, 8: 89-93 (Year: 1995).*
Rudikoff, S., Giusti, A. M., Cook, W. D., and Scharff, M. D., Single amino acid substitution altering antigen-binding specificity, Mar. 1982, Proc. Natl. Acad. Sci. USA, 79: 1979-1983 (Year: 1982).*
Machine Translation for CN 110423726 A (2019).
Ma et al. (2019). The Spodoptera frugiperda Sf9 cell line is a heterogeneous population of rhabdovirus-infected and virus negative cells: Isolation and characterization of cell clones containing rhabdovirus X-gene variants and virus-negative cell clones. Virology, 536, 125-133.
Maghodia et al. (2016). Characterization of an Sf-rhabdovirus-negative Spodoptera frugiperda cell line as an alternative host for recombinant protein production in the baculovirus-insect cell system. Protein Expr Purif. Jun. 2016;122:45-55. doi: 10.1016/j.pep.2016.02.014. Epub Feb. 23, 2016. Erratum in: Protein Expr Purif. Dec. 8, 2017;144:39. Erratum in: Protein Expr Purif. Jan. 2019;153:44. PMID: 26923062; PMCID: PMC4842140.

(Continued)

*Primary Examiner* — Michael Allen
*Assistant Examiner* — Kristina E. Ly
(74) *Attorney, Agent, or Firm* — CAESAR RIVISE, PC

(57) ABSTRACT

The invention pertains to the technical fields of genetic engineering and cell engineering, and in particular relates to a rhabdovirus-negative *Spodoptera frugiperda* insect cell line, and screening, identification and application thereof. According to the invention, the rhabdovirus-negative *Spodoptera frugiperda* insect cell line WSK-Sf9, with a CCTCC accession number C202246, is obtained through screening and identification. The cell line is verified through various high-sensitivity test methods such as nested PCR, transcriptome next-generation sequencing, real-time fluorescence quantitative PCR and TAQMAN probe-based real-time PCR, and finally obtained the Sf-rhabdovirus-negative *Spodoptera frugiperda* insect cell line WSK-Sf9. The cell is tested for sterility, mycoplasma, exogenous virus and tumorigenicity according to pharmacopeial requirements, and the results show that all indicators satisfy the requirements, and the cell can be used in or for the production of recombinant proteins and recombinant protein vaccines based on the baculovirus expression system.

12 Claims, 4 Drawing Sheets

Specification includes a Sequence Listing.

(56) References Cited

OTHER PUBLICATIONS

Xu et al. (2020). The discovery of viruses associated with the fall armyworm Spodoptera frugiperda by high-throughput sequencing. Journal of Plant Protection, 47(4), 807-814 with English Abstract.
Screenshot captured from http://www.glycobac.com/sf-rvn-cells on Oct. 6, 2023.
Translation of International Search Report for PCT/CN2022/141358 dated Mar. 2, 2023.

* cited by examiner

SEQUENCE LISTING

```
Sequence total quantity: 11
SEQ ID NO: 1           moltype = DNA  length = 22
FEATURE                Location/Qualifiers
source                 1..22
                       mol_type = other DNA
                       organism = synthetic construct
SEQUENCE: 1
aggagaactc caaagactca gc                                              22

SEQ ID NO: 2           moltype = DNA  length = 20
FEATURE                Location/Qualifiers
source                 1..20
                       mol_type = other DNA
                       organism = synthetic construct
SEQUENCE: 2
aaaaggagtc cccactcagc                                                 20

SEQ ID NO: 3           moltype = DNA  length = 20
FEATURE                Location/Qualifiers
source                 1..20
                       mol_type = other DNA
                       organism = synthetic construct
SEQUENCE: 3
ccacatctcc gctatcacca                                                 20

SEQ ID NO: 4           moltype = DNA  length = 19
FEATURE                Location/Qualifiers
source                 1..19
                       mol_type = other DNA
                       organism = synthetic construct
SEQUENCE: 4
aggagaagga gcggttgga                                                  19

SEQ ID NO: 5           moltype = DNA  length = 20
FEATURE                Location/Qualifiers
source                 1..20
                       mol_type = other DNA
                       organism = synthetic construct
SEQUENCE: 5
tgaaaacctt cgcacagcac                                                 20

SEQ ID NO: 6           moltype = DNA  length = 20
FEATURE                Location/Qualifiers
source                 1..20
                       mol_type = other DNA
                       organism = synthetic construct
SEQUENCE: 6
cgagacccct ttggaccttt                                                 20

SEQ ID NO: 7           moltype = DNA  length = 20
FEATURE                Location/Qualifiers
source                 1..20
                       mol_type = other DNA
                       organism = synthetic construct
SEQUENCE: 7
ggattgcacg gagcctatca                                                 20

SEQ ID NO: 8           moltype = DNA  length = 20
FEATURE                Location/Qualifiers
source                 1..20
                       mol_type = other DNA
                       organism = synthetic construct
SEQUENCE: 8
tgcccaagct aaggaaaggg                                                 20

SEQ ID NO: 9           moltype = DNA  length = 20
FEATURE                Location/Qualifiers
source                 1..20
                       mol_type = other DNA
```

-continued

```
                       organism = synthetic construct
SEQUENCE: 9
tgacatgtgg tctccaaccg                                              20

SEQ ID NO: 10          moltype = DNA  length = 20
FEATURE                Location/Qualifiers
source                 1..20
                       mol_type = other DNA
                       organism = synthetic construct
SEQUENCE: 10
gtatgcaggt ggttgaggct                                              20

SEQ ID NO: 11          moltype = DNA  length = 21
FEATURE                Location/Qualifiers
source                 1..21
                       mol_type = other DNA
                       organism = synthetic construct
SEQUENCE: 11
ctccttctcc tccacccaca t                                            21
```

RHABDOVIRUS-NEGATIVE SPODOPTERA FRUGIPERDA INSECT CELL LINE, AND SCREENING, IDENTIFICATION AND APPLICATION THEREOF

CROSS-REFERENCE TO RELATED APPLICATIONS

This application is a U.S. National Phase Application of PCT/CN2022/141358, filed Dec. 23, 2022, which claims priority to CN 202210194024.X, filed Mar. 1, 2022, the contents of which applications are incorporated herein by reference in their entireties for all purposes.

SEQUENCE LISTING STATEMENT

Incorporated herein by reference in its entirety is a Sequence Listing named "C127820072_SEQUENCE LISTING", submitted to the USPTO on Oct. 20, 2023 via the USPTO patent electronic filing system as an XML file 11 KB in size. This file, which was created on Aug. 29, 2023, constitutes both the paper and computer readable form of the Sequence Listing.

TECHNICAL FIELD

The invention pertains to the technical fields of genetic engineering and cell engineering, and relates to a new *Spodoptera frugiperda* insect cell line, and in particular relates to a rhabdovirus-negative *Spodoptera frugiperda* insect cell line and screening, identification and application thereof.

BACKGROUND OF THE RELATED ART

Insect cell expression system has been widely used in the production of recombinant protein and has many advantages as compared to other expression systems. For example, as insect baculovirus is parasitic only on invertebrates, the expression system has high safety and high expression level of recombinant protein, and can correctly fold and modify the recombinant protein after translation to obtain a protein with biological activity, and the insect cell expression system is adapted to the complex design of multi-gene expression such as virus-like particles and can be applied to large-scale serum-free culture and the like.

At present, multiple recombinant protein vaccines produced by the insect cell expression system have demonstrated good effects and safety, and have been approved for listing worldwide, including CERVARIX cervical cancer vaccine produced by GSK, PROVENGE prostate cancer vaccine produced by Dendreon, and FLUBLOK influenza vaccine produced by ProteinSciences. Moreover, many recombinant protein vaccines in the preclinical experimental stage have also demonstrated good prospects for application.

Sf9 cell (*Spodoptera frugiperda* cell) is the most commonly used insect cell in the insect baculovirus expression system to express and produce foreign proteins, including antibodies, vaccines and recombinant proteins. Sf9 cells are derived from an IPLBSF-21 cell line (also called Sf21), which is originated from the ovarian tissue of autumn fly worm (*Spodoptera frugiperda*) pupae isolated and cultured in 1977. Sf-rhabdovirus is a new negative-strand RNA virus discovered by FDA researchers in 2014 in the *Spodoptera frugiperda* cell line Sf9 and its parent cell line Sf21, including gene information of structural proteins of N, P, M, G and L. In addition, an extra gene sequence X with unknown function between G and L was tested. Although Sf-rhabdovirus is not integrated into the genome of host cells, it has a complete genome and may be packaged into a complete virus particle, which has potential risks to the production and use of recombinant proteins such as vaccines obtained based on the baculovirus expression system of Sf9 cells.

BRIEF SUMMARY OF THE INVENTION

According to the invention, a rhabdovirus-negative *Spodoptera frugiperda* insect cell line WSK-Sf9 (abbreviated as WSK-Sf9) is obtained through screening and identification, and the cell line can be used for the production of recombinant proteins and recombinant protein vaccines based on a baculovirus expression system.

An objective of the invention is to provide a rhabdovirus-negative *Spodoptera frugiperda* insect cell line WSK-Sf9, with a CCTCC accession number C202246. The cell line was collected with a name of *Spodoptera frugiperda* Sf9-derived cell line WSK-Sf9 on Feb. 16, 2022. The Collection Center is China Center for Type Culture Collection (CCTCC) and its address is Wuhan University Collection Center, No. 299 Bayi Road, Wuchang District, Wuhan City, Hubei Province, with a zip code of 430072.

The rhabdovirus-negative *Spodoptera frugiperda* insect cell line WSK-Sf9 of the invention is characterized in that a monoclonal cell is screened by using a limited dilution method, verified through various high-sensitivity test methods such as nested PCR, transcriptome next-generation sequencing, real-time fluorescence quantitative PCR and TAQMAN probe-based real-time PCR, and then obtained the rhabdovirus-negative *Spodoptera frugiperda* insect cell line WSK-Sf9. The cell is tested for sterility, mycoplasma, exogenous virus and tumorigenicity according to pharmacopeial requirements, and the results show that all indicators satisfy the requirements, and the cell can be used as a cell matrix for production.

Another objective of the invention is to provide an application of the rhabdovirus-negative *Spodoptera frugiperda* insect cell line WSK-Sf9 in production of a recombinant protein based on a baculovirus expression system.

The application includes an application of production of a recombinant protein medicine or vaccine based on the baculovirus expression system.

The recombinant protein medicine includes a cytokine, a hormone, a recombinant enzyme or an antibody.

The cytokine includes a recombinant human interleukin, a recombinant human epidermal growth factor, a recombinant human interferon, a recombinant human fibroblast growth factor, a recombinant human erythropoietin or a recombinant human granulocyte macrophage stimulating factor.

The hormone includes a recombinant human growth hormone, a recombinant human insulin, an insulin analog or a recombinant human follicle maturing hormone.

The recombinant enzyme includes a recombinant human alpha-glucosidase or a recombinant human prourokinase.

The antibody includes a monoclonal antibody, a Fab antibody, a scFv antibody or a nanobody.

The vaccine includes a recombinant protein vaccine or a virus-like particle vaccine.

The recombinant protein vaccine includes a SARS-COV-2 protein vaccine, an influenza virus protein vaccine, a syncytial virus recombinant protein vaccine, a hepatitis B virus protein vaccine or a rabies virus protein vaccine, and preferably the SARS-COV-2 protein vaccine.

The virus-like particle vaccine includes a SARS-COV-2 virus-like particle vaccine (SARS-COV-2-VLP), a human papillomavirus-like particle vaccine (HPV-VLP), an influenza virus-like particle vaccine (HA-VLP), a poliovirus-like particle vaccine (PV-VLP), a respiratory syncytial virus-like particle vaccine (RSV-VLP) or a hand-foot-mouth disease virus-like particle vaccine (EV71-VLP). Preferably, the virus-like particle vaccine is the SARS-COV-2 virus-like particle vaccine.

A technical solution for realizing an application of WSK-Sf9 in the production of recombinant protein or vaccine based on the baculovirus expression system is that: A BAC-TO-BAC insect baculovirus expression system is used to package and produce baculovirus and infect WSK-Sf9 cells to express a target protein, so that a target recombinant protein is obtained by an affinity purification technology.

The beneficial effect of the invention is that: A monoclonal cell is screened by using a limited dilution method, verified through various high-sensitivity test methods such as nested PCR, transcriptome next-generation sequencing, real-time fluorescence quantitative PCR and TAQMAN probe-based real-time PCR, and then obtained the rhabdovirus-negative *Spodoptera frugiperda* insect cell line WSK-Sf9. The cell is tested for sterility, mycoplasma, exogenous virus and tumorigenicity according to pharmacopeial requirements, and the results show that all indicators satisfy the requirements, and the cell can be used for production of recombinant protein products such as protein vaccines for clinical use. In addition, according to the invention, the BAC-TO-BAC insect baculovirus expression system is used to package and produce baculovirus and infect WSK-Sf9 cells to express the target protein, so that the target recombinant protein is obtained by the affinity purification technology or other technical ways.

According to the invention, the rhabdovirus-negative *Spodoptera frugiperda* insect cell line WSK-Sf9 obtained through screening and identification has a CCTCC accession number C202246. The cell line was collected on Feb. 16, 2022. The Collection Center is China Center for Type Culture Collection (CCTCC) and its address is Wuhan University Collection Center, No.299 Bayi Road, Wuchang District, Wuhan City, Hubei Province, with a zip code of 430072. The name and identification characteristics of the collected culture are *Spodoptera frugiperda* Sf9-derived cell line WSK-Sf9.

DETAILED DESCRIPTION OF THE EMBODIMENTS OF THE INVENTION

Figure 1:
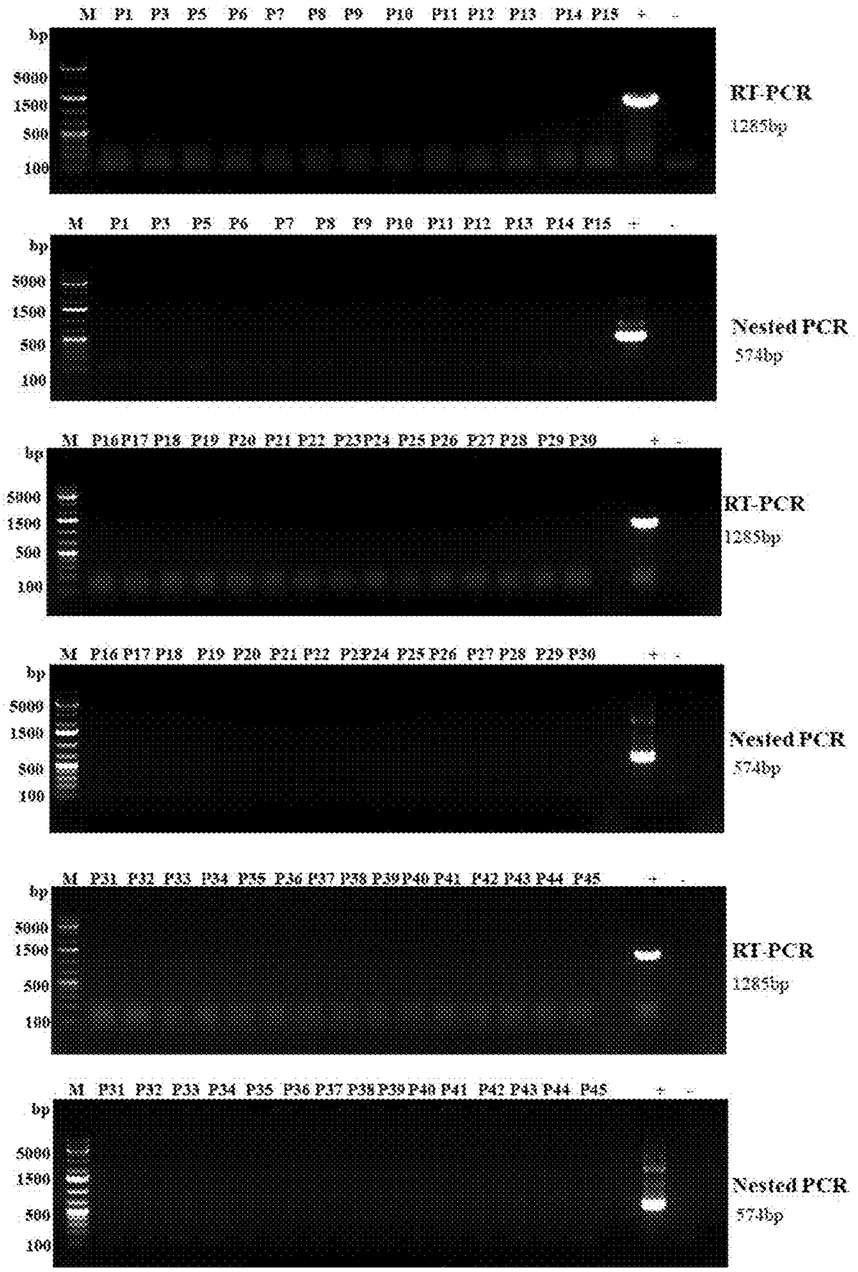
FIG. 1 shows the result of nested PCR agarose gel electrophoresis for identification of WSK-Sf9 cells according to the invention.

The following will explain the solutions of the present invention with reference to specific embodiments. A person skilled in the art will understand that the following embodiments are intended to illustrate the invention only and should not be considered as limiting the scope of the invention. In case that specific technologies or conditions are not specified in the embodiments, technologies or conditions described in the literature in the art or the product specification shall prevail. If a manufacturer is not indicated in reagents or instruments used, they are all conventional products that can be purchased from the commercial reagent companies.

The screening, identification and application of the rhabdovirus-negative Spodoptera frugiperda insect cell line WSK-Sf9 will be further illustrated in the following embodiments, and the invention will be further described with reference to the attached drawings.

Embodiment 1: Screening and Identification of Sf-rhabdovirus-negative *Spodoptera frugiperda* Insect Cell Line WSK-Sf9

The only commercially available Sf-rhabdovirus-negative Sf-RVN cells (Sf-rhabdovirus-negative Sf9) were screened from Sf9 by Prof. Jarvis' team through a limited dilution method combined with antiviral drug treatment (Maghodia AB, et al. *Protein expression and purification*. 2016;122: 45-55.), and verified to be Sf-rhabdovirus-negative by nested PCR for an L gene, and the cells are attributed to GlycoBac (glycobac.com/sf-rvn-cells) which has entered into a partnership with Millipore/Sigma Inc. to entrust Millipore/Sigma to sell them.

According to non-patent references: "Ma H, Nandakumar S, Bae E H, Chin P J, Khan A S, the *Spodoptera frugiperda* Sf9 cell line is a heterogeneous population of rhabdovirus-infected and virus-negative cells: Isolation and characterization of cell clones containing rhabdovirus X-gene variants and virus-negative cell clones. According to *Virology* 2019;536:125-33", *Spodoptera frugiperda* Sf9 cell line is a heterogeneous cell population, which includes two types of cell populations: Sf-rhabdovirus-infected cells and Sf-rhabdovirus-negative cells. A single Sf-rhabdovirus-negative cell population can be obtained by the limited dilution method. According to the invention, a monoclonal cell is selected by the limited dilution method, and then Sf-rhabdovirus-negative cells are screened and identified by methods such as nested PCR, transcriptome next-generation sequencing, real-time fluorescence quantitative PCR and TAQMAN probe-based real-time PCR and the like.

1) The parental cell line of Sf9 was purchased from ThermoFisher Company (Lot No .: 2043331), and the purchased cells were defined as passage zero (P0). The passage used in this screening experiment was passage 4 (P4), and the cell culture medium was SIM SF serum-free medium (Sino Biological, Inc., MSF1). The suspended Sf9 cells were diluted in a 10-times gradient and plated onto well plates, and the cells were observed every a few days. When distinct monoclonal cells became noticeable, they were transferred to a new well plate for expansion. Then, appropriate cells were collected, total RNA was extracted, and candidate cells were preliminarily identified by a nested PCR primer (Table 1) for Sf-rhabdovirus specific M gene.

TABLE 1

| Nested PCR primer sequence information for Sf-rhabdovirus specific M gene | | |
|---|---|---|
| Primer name | Primer sequence (5' to 3') | Primer amplification zone nt |
| Sf-M-NEST-01-for | AGGAGAACTCCAAAGACTCAGC (SEQ ID NO. 1) | 3142-4426 |
| Sf-M-NEST-01-for | AAAAGGAGTCCCCACTCAGC (SEQ ID NO. 2) | |
| Sf-M-NEST-02-for | CCACATCTCCGCTATCACCA (SEQ ID NO. 3) | 3240-3813 |
| Sf-M-NEST-02-rev | AGGAGAAGGAGCGGTTGGA (SEQ ID NO. 4) | |

2) The candidate Sf-rhabdovirus-negative cells were continuously subcultured, and cell samples were collected and frozen at −80° C. for later use. After 45 passages of continuous culture, the nested PCR technology was used to detect the cell samples, and the results showed that Sf-rhabdovirus M genes in P1-P45 of the WSK-Sf9 were consistently negative (FIG. 1).

3) Transcriptome next-generation sequencing: $5*10^6$ parental Sf9 cells and $5*10^6$ WSK-Sf9 cells were collected separately for next-generation sequencing, and the results showed that the RNA gene information of Sf-Rhabdovirus was detected in the transcriptome of the parental Sf9 cells (GenBank: KF947078.1), but not in that of WSK-Sf9 cells.

4) Realtime fluorescence quantitative PCR: Two pairs of quantitative PCR primers for Sf-rhabdovirus M genes were designed (Table 2), a Bio-Rad SSOFASTE-VAGREENSUPERMIX kit was used for fluorescence quantitative PCR test, and the results showed that no fluorescence signal was detected in WSK-Sf9 P3 generation and P28 generation, proving that the WSK-Sf9 cells were Sf-rhabdovirus-negative (Table 3).

TABLE 2

| Specific Q-PCR primer for Sf-rhabdovirus M gene | | |
|---|---|---|
| Primer name | Primer sequence (5' to 3') | Primer amplification zone nt |
| SFV-M1-qPCR-for | TGAAAACCTTCGCACAGCAC (SEQ ID NO. 5) | 3566-3752 |
| SFV-M1-qPCR-rev | CGAGACCCCTTTGGACCTTT (SEQ ID NO. 6) | |
| SFV-M2-qPCR-for | GGATTGCACGGAGCCTATCA (SEQ ID NO. 7) | 3104-3291 |
| SFV-M2-qPCR-rev | TGCCCAAGCTAAGGAAAGGG (SEQ ID NO. 8) | |

TABLE 3

| Q-PCR experimental data Ct value | | | | |
|---|---|---|---|---|
| | WSK-Sf9 P3 | WSK-Sf9 P28 | Sf9 (+) | $H_2O$(−) |
| M1 | N.D. | N.D. | 19.76 | N.D. |
| M1 | N.D. | N.D. | 19.74 | N.D. |
| M1 | N.D. | N.D. | 19.75 | N.D. |
| M2 | N.D. | N.D. | 19.12 | N.D. |
| M2 | N.D. | N.D. | 19.23 | N.D. |
| M2 | N.D. | N.D. | 19.13 | N.D. |

Note:
the data in the table 3 represents the results of three replicate samples.

5) Quantitative PCR by probe method: A TAQMAN probe for Sf-rhabdovirus M genes was designed (Table 4), and the results of quantitative PCR showed that no fluorescence signal was tested in a main cell bank (MCB) and a working cell bank (WCB) of WSK-Sf9, proving that the WSK-Sf9 cells were Sf-rhabdovirus-negative (Table 5).

TABLE 4

| Specific TAQMAN probe primer for Sf-rhabdovirus M gene | | | | |
|---|---|---|---|---|
| Primer name | Primer sequence (5' to 3') | Modified | | Primer amplification zone nt |
| Sf-taqM-F | TGACATGTGGTCTCCAACCG (SEQ ID NO. 9) | — | — | 3783-3887 |
| Sf-taqM-R | GTATGCAGGTGGTTGAGGCT (SEQ ID NO. 10) | — | — | |
| Sf-taqM-pro | CTCCTTCTCCTCCACCCACAT (SEQ ID NO. 11) | 5'-FAM | 3'-MGB | |

TABLE 5

| TAQMAN Q-PCR experimental data Ct value | | | |
|---|---|---|---|
| WSK-Sf9 MCB | WSK-Sf9 WCB | Sf9 (+) | $H_2O$(−) |
| N.D. | N.D. | 20.96 | N.D. |
| N.D. | N.D. | 20.53 | N.D. |
| N.D. | N.D. | 20.77 | N.D. |

Note:
the data in the table 5 represents the results of three replicate samples.

Embodiment 2: Growth Characteristics of Sf-rhabdovirus-negative *Spodoptera frugiperda* Insect Cell Line WSK-Sf9

Figure 2:
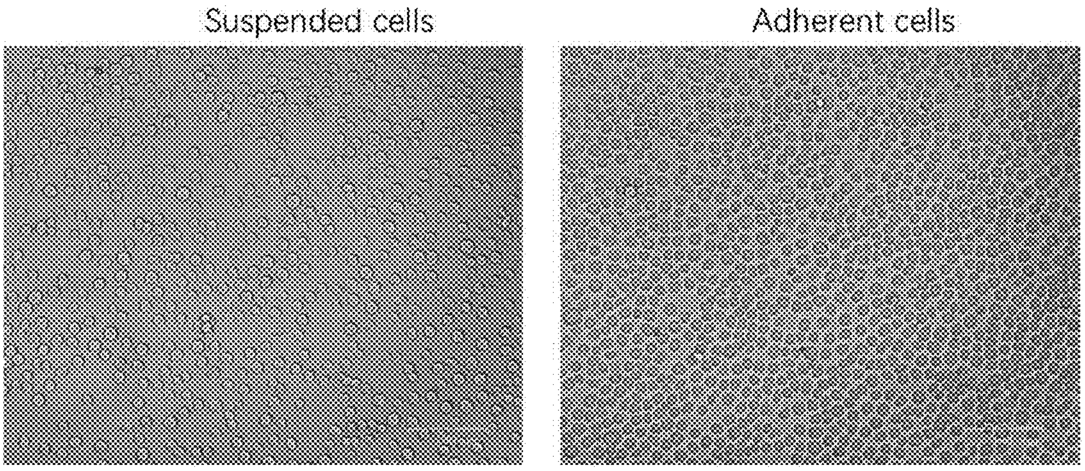
FIG. 2 shows the morphological characteristics of the rhabdovirus-negative *Spodoptera frugiperda* insect cell line WSK-Sf9 obtained through screening according to the invention.
Figure 3:
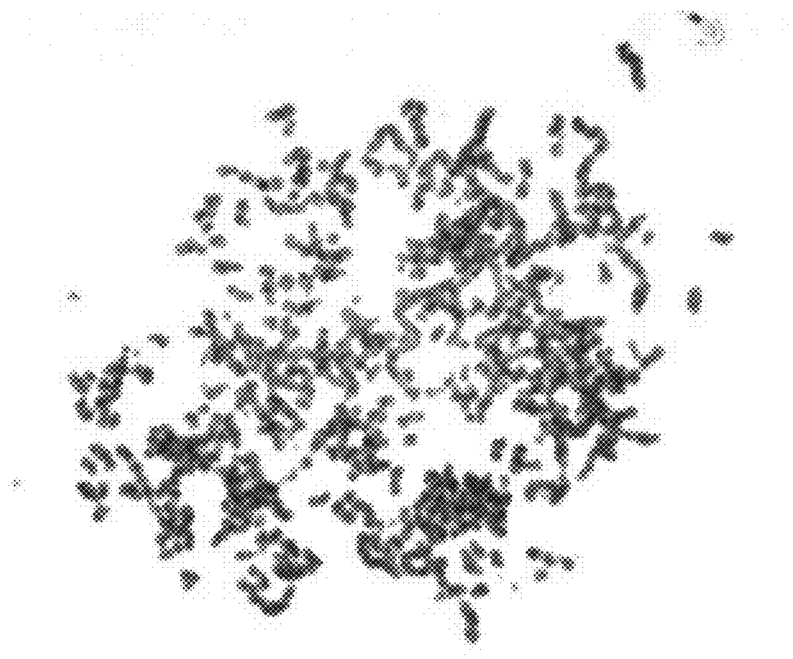
FIG. 3 shows the karyotype analysis of the rhabdovirus-negative *Spodoptera frugiperda* insect cell line WSK-Sf9 obtained through screening according to the invention.
Figure 4:
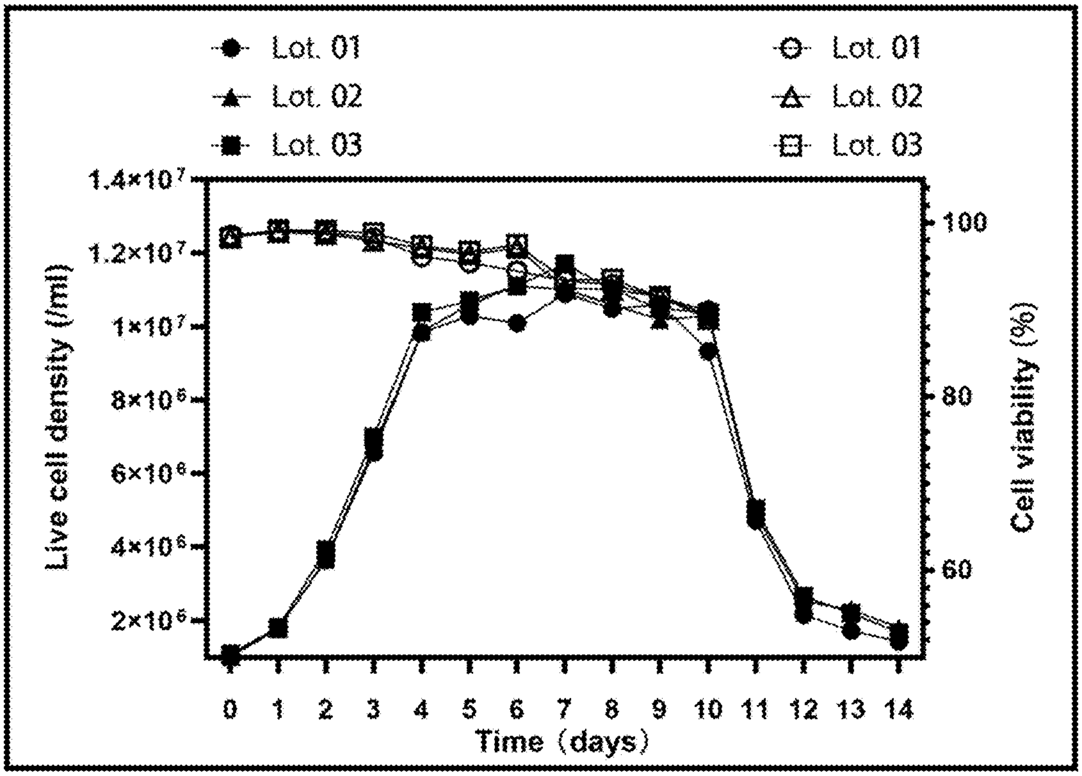
FIG. 4 shows a growth curve of the rhabdovirus-negative Spodoptera frugiperda insect cell line WSK-Sf9 obtained through screening according to the invention.
Figure 5:
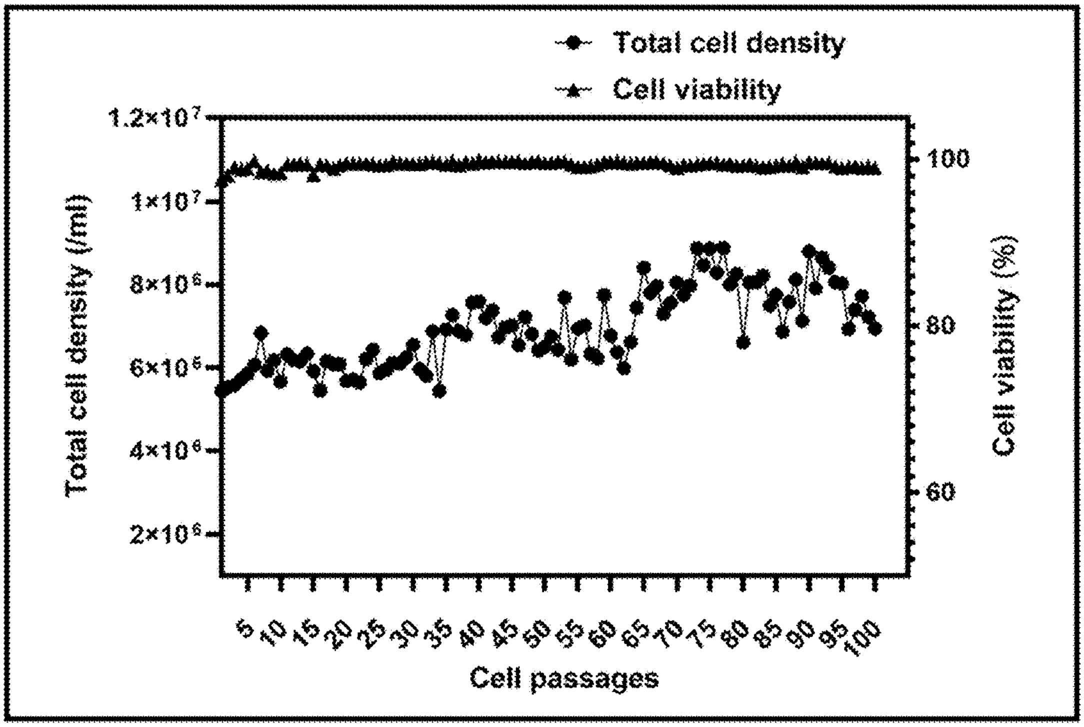
FIG. 5 shows a continuous subculturing curve of the rhabdovirus-negative *Spodoptera frugiperda* insect cell line WSK-Sf9 obtained through screening according to the invention.
Figure 6:
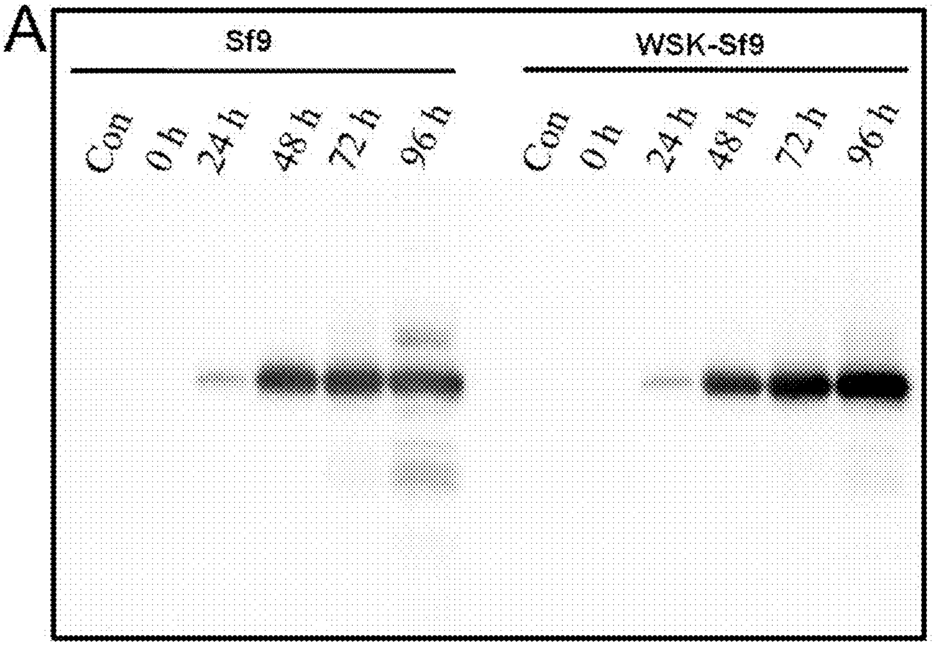
FIG. 6 shows a time gradient test of an exogenous recombinant protein expressed by the rhabdovirus-negative *Spodoptera frugiperda* insect cell line WSK-Sf9 obtained through screening according to the invention.
Figure 6:
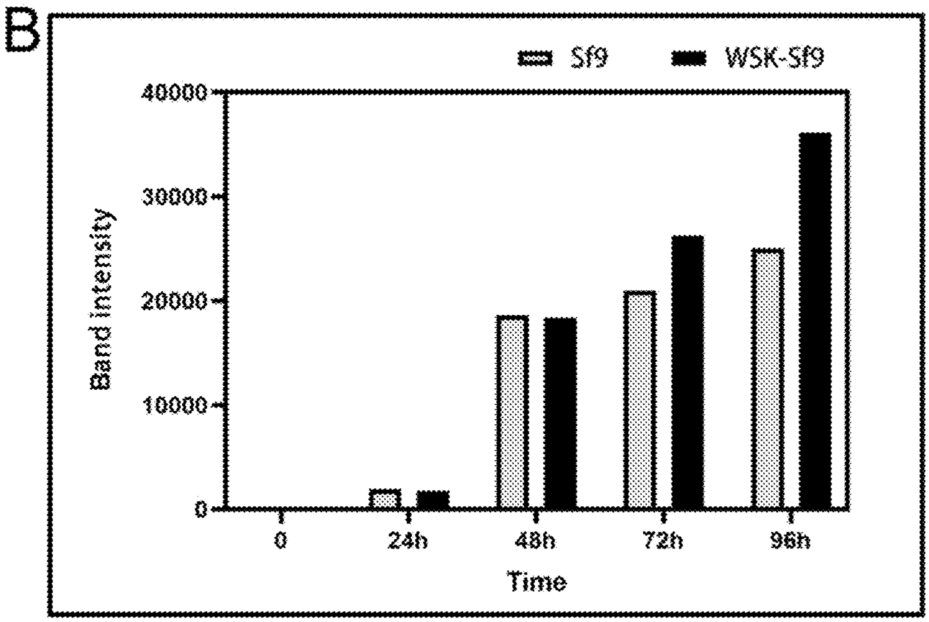

1) Culture characteristics of WSK-Sf9: The cell could grow in a serum-free medium at 27° C. in a way of adherence or suspension, with an average diameter in suspension growth of 16.28±0.34 μm and morphological characteristics of WSK-Sf9 as shown in FIG. 2
2) Karyotype analysis of WSK-Sf9: A karyotype analysis was carried out on the parental Sf9 cells, and the results showed that among 60 metaphase cells, the number of chromosomes was mainly distributed between 180-250, with an average of 215 chromosomes per cell; Meanwhile, karyotype analysis was also carried out on WSK-Sf9 cells, and the results showed that among 60 metaphase cells, the number of chromosomes was mainly distributed between 191-538, with an average of 299 chromosomes per cell (FIG. 3). This also means that the Sf-rhabdovirus-negative cell line WSK-Sf9 is different from its parental Sf9 cells.
3) WSK-Sf9 cell growth curve: WSK-Sf9 cells in logarithmic growth phase were diluted to approximately $1\times10^6$ cells/ml and passaged into 250 ml vented shake flasks. The cultivation volume was 100 ml, and the flasks were placed in a constant temperature shaker at 27° C. for continuous cultivation. Cell density and viability were counted every 24 hours. After three different batches of cultivation, the growth curve and viability are shown in FIG. 4. The cell density reached approximately $1\times10^7$ cells/ml after 96 hours and remained at this level for 6 days. The highest cell density approached $1.2\times10^7$ cells/ml, and the cell viability gradually decreased from the 11th day, and the average doubling time was around 23 hours.
4) Continuous subculturing curve of WSK-Sf9 cells: WSK-Sf9 cells in logarithmic growth phase were diluted to approximately $1\times10^6$ cells/ml and passaged into 250 ml vented shake flasks. The cultivation volume was 100 ml, and the flasks were placed in a constant temperature shaker at 27° C. for continuous cultivation. Cell density and viability were counted every 3 days, and passaging was performed. Generally, after 3 days of cultivation, the cell density could reach $6\sim8\times10^6$ cells/ml, with a viability of over 98%. The continuous subculturing growth curve and viability are shown in FIG. 5. After 100 consecutive passages, the cell growth characteristics remained stable.

Embodiment 3: Safety Test of Sf-rhabdovirus-negative *Spodoptera frugiperda* Insect Cell Line WSK-Sf9

The following tests were conducted on WSK-Sf9 cells according to Part III of *China Pharmacopoeia* (Edition 2020).

1) Species identification: A DNA Barcoding method was used to detect the WSK-Sf9 cells, and the results showed that the WSK-SF9 cells were from the Spodoptera frugiperda;
2) Aseptic test: A membrane filtration method was adopted to carry out the aseptic test, and the results showed that the growth of the WSK-Sf9 cells was aseptic;
3) Mycobacterium test: A culture method was adopted to test mycobacterium, and the results showed that mycobacterium was negative;
4) Mycoplasma test: A culture method, an indicator cell culture method and a Touchdown PCR method were adopted to test mycoplasma, and the results showed that mycoplasma was negative;
5) Spiroplasma test: A fluorescence PCR method was adopted to test spiroplasma, and the results showed that spiroplasma was negative;
6) Exogenous virus test:
   (1) An in vitro cell observation method, an erythrocyte adsorption test and hemagglutination inhibition test were adopted to test subculturing of different cells of monkey-derived Vero cells, human MRC-5 cells, Sf9 cells, BHK-21 cells, mosquito-derived cells Aedes and *Drosophila*-derived cells D.Mel, and all the cells showed normal morphology and tested negative.
   (2) Suckling mice, adult mice and chicken embryos (5-6 days old chicken embryos and 9-11 days old chicken embryos) were inoculated by the in vivo method, and the results showed that they all satisfied the requirements.
7) Retrovirus test: No virus-like particles were found by a transmission electron microscope, a HEK293 cell inoculation subculturing infection test and chemical reagent induced virus test, and the results showed that they all satisfied the requirements;
8) The cells in bovine-derived virus test and pig-derived virus test were negative;
9) Other specific viruses were tested, including Baculoviruses, T.ni flock house virus variant (FHVvar), Rhabdoviruses, Reoviridae, Togaviruses, Flaviviruses, Bunyaviruses, Asfaviruses, Ascoviridae, Iridoviridae, Poxviridae, Baculoviridae, Poldnaviridae, Parvoviridae, Birnaviridae, Reoviridae, Picornaviralses, Dicistrovitidae, Nodaviridae and Tetraviridae; and the results showed that they were all negative and satisfied the requirements.
10) Tumorigenicity test: Experimental mice were inoculated with the WSK-Sf9 cells, and the results showed that the cells were not tumorigenic and could satisfy the requirements.

In conclusion, the Sf-rhabdovirus-negative *Spodoptera frugiperda* insect cell line WSK-Sf9 satisfies the requirements for all safety tests and the requirements for cellular matrices for the production of biologics.

Embodiment 4: Exogenous Recombination Protein Expressed by Sf-rhabdovirus-negative *Spodoptera frugiperda* Insect Cell Line WSK-Sf9

A baculovirus expression vector containing an RBD structural domain of SARS-COV-2 was constructed, and WSK-Sf9 cells were used to package the recombinant protein-expressing baculovirus. Sf9 and WSK-Sf9 cells were cultured separately; when the density reached $2.5\times10^6$/ml, they were infected separately with viruses at a ratio of MOI=0.5.Supernatants were collected before infection (0 hr) and after infection ($24^{th}$ hr, $48^{th}$ hr, $72^{nd}$ hr, and $96^{th}$ hr), which were detected by western-blot using antibodies against the His tag, and the results showed that the expression level of the recombinant protein in the WSK-Sf9 cells was up-regulated as compared to that in the Sf9 cells. After production and purification in a GMP workshop and subsequent adjuvant formulation, the recombinant protein can be used to prevent infection of SARS-COV-2. This demonstrates that the Sf-rhabdovirus-negative *Spodoptera frugiperda* insect cell line WSK-Sf9 can be used to express and produce exogenous recombinant proteins such as protein vaccines, and the expression level is higher than the Sf9 cells.

The invention claimed is:

1. A Rhabdovirus-negative *Spodoptera frugiperda* insect cell line WSK-Sf9 with a China Center for Type Culture Collection (CCTCC) accession number C202246.

2. A method for producing a composition comprising a recombinant protein, said method comprising expressing the recombinant protein using the Rhabdovirus-negative Spodoptera frugiperda insect cell line WSK-Sf9 according to claim 1.

3. The method according to claim 2, wherein the composition is a medicine or a vaccine.

4. The method according to claim 2, wherein the recombinant protein is a cytokine, a hormone, or a recombinant enzyme.

5. The method according to claim 4, wherein the cytokine is selected from the group consisting of a recombinant human interleukin, a recombinant human epidermal growth factor, a recombinant human interferon, a recombinant human fibroblast growth factor, a recombinant human erythropoietin, and a recombinant human granulocyte macrophage stimulating factor.

6. The method according to claim 4, wherein the hormone is selected from the group consisting of a recombinant human growth hormone, a recombinant human insulin, an insulin analog, and a recombinant human follicle maturing hormone.

7. The method according to claim 4, wherein the recombinant enzyme is selected from the group consisting of a recombinant human alpha-glucosidase and a recombinant human prourokinase.

8. The method according to claim 2, wherein the recombinant protein is selected from the group consisting of a SARS-COV-2 protein, an influenza virus protein, a syncytial virus recombinant protein, a hepatitis B virus protein, and a rabies virus protein.

9. The method according to claim 3, wherein the vaccine comprises a virus-like particle vaccine selected from the group consisting of a SARS-COV-2 virus-like particle vaccine, a human papillomavirus-like particle vaccine, an influenza virus-like particle vaccine, a poliovirus-like particle vaccine, a respiratory syncytial virus-like particle vaccine, and a hand-foot-mouth disease virus-like particle vaccine, wherein each virus-like particle vaccine comprises the recombinant protein.

10. The method according to claim 8, wherein the recombinant protein is a SARS-COV-2 protein.

11. The method according to claim 9, wherein the virus-like particle vaccine is a SARS-COV-2 virus-like particle vaccine.

12. The method according to claim 2, wherein the composition consists of the recombinant protein.

* * * * *